United States Patent [19]

Harmer

[11] 4,433,913

[45] Feb. 28, 1984

[54] REFRACTIVE INDEX OF A LIQUID REFERRED TO A PREDETERMINED TEMPERATURE

[75] Inventor: Alan L. Harmer, Plan les Ouattes, Switzerland

[73] Assignee: Battelle Memorial Institute, Switzerland

[21] Appl. No.: 343,698

[22] Filed: Jan. 28, 1982

[30] Foreign Application Priority Data

Jan. 30, 1981 [CH] Switzerland .................. 611/81

[51] Int. Cl.³ .................................. G01N 21/43
[52] U.S. Cl. ............................... 356/133; 374/130; 250/331 R
[58] Field of Search ............... 356/128, 130, 131, 133, 356/135, 136; 374/130, 731

[56] References Cited

U.S. PATENT DOCUMENTS 3,282,149 11/1966 Shaw et al. ...................... 356/133
4,187,025 2/1980 Harmer ........................... 356/133
4,256,403 3/1981 Powell ............................ 356/133

*Primary Examiner*—R. A. Rosenberger
*Attorney, Agent, or Firm*—Karl F. Ross

[57] ABSTRACT

An apparatus or device for determining the index of refraction of a fluid referred to or reduced to a predetermined reference temperature comprises a light source, light detector and means forming a bent light-conducting path between the source and the detector such that the intensity of the detected illumination represents the refractive index of the fluid surrounding the light-conductive path. According to the invention, the light source comprises an electroluminescent diode, e.g. a light-emitting diode of the LED type which has a temperature coefficient in conjunction with the temperature coefficient of the optical fiber which compensates substantially precisely for veriations in the temperature coefficient of the effective index and the fluid with which both the path and the LED are in thermally conducting relation, e.g. in direct contact.

5 Claims, 3 Drawing Figures

REFRACTIVE INDEX OF A LIQUID REFERRED TO A PREDETERMINED TEMPERATURE

CROSS REFERENCE TO RELATED APPLICATION

The present application is related to my copending application Ser. No. 303,083 filed Sept. 17, 1981 and based upon a Swiss application 6698/80-4 of Sept. 18, 1980.

FIELD OF THE INVENTION

My present invention relates to the determination of the refractive index of a fluid and, more particularly, to an apparatus or device for measuring the refractive index of a fluid, especially a liquid, referred to or reduced to a predetermined temperature (hereinafter the reference temperature) in spite of the fact that the measurements may be taken at temperatures differing from the reference temperature.

BACKGROUND OF THE INVENTION

Measurements of fluid refractive index are highly valued as indicia of the composition of the liquid and other characteristics thereof and the index of refraction is known to have temperature dependency so that, for making a comparison of refractive index measurements, it is necessary to modify the measured value by reducing it or referring it back to a predetermined reference temperature, e.g. 20° C. ("room temperature").

Thus, it is known to provide a refractometer for determining the index of refraction of a liquid which utilizes the reflection and refraction phenomena occurring at the interface between a light-conductive path andd the liquid close to the critical angle which is a function of the index of refraction of the fluid.

Earlier refractometers utilizing this principle are relatively simple and precise instruments. In general, they may comprise an optical detector, a light source and a light-conductive structure connecting the detector with the source and of a configuration (curvature in alternate senses) such that internal reflection and refraction is induced along the light path between the input end and the output end thereof. Because the sensor responds only to the light reaching the sensor along the path and not the light which, because of the critical angle, passes into the liquid, the light intensity at the detector is a function of the critical angle and hence a measure of the index of refraction at the particular temperature of the liquid. This light intensity can be converted by the detector into an output signal whose value represents the measured index of refraction.

The means forming the light conductive path is immersed in the liquid whose index of refraction is to be measured.

The measured index of refraction with such a probe is the true index of refraction and is a function of two parameters. One parameter is the light bending characteristic of the liquid, a parameter which is dependent upon physical properties of the liquid, while the other parameter is the temperature.

The true index of refraction can seldom be utilized unless the temperature at the point of measurement is also known or ascertained. In most common cases, both values must be obtained to allow separation of the part of the index which is due to refraction proper and the physical properties of the liquid and which part may be due to temperature.

It should be apparent that comparison of refractive indices obtained in this manner, to permit deductions about relative compositions of liquids or the like, is seldom possible unless both indices have been measured at precisely the same temperature.

It is a common practice, therefore, utilizing empirically derived equations for the temperature coefficient of the index of refraction to reduce a measured value of an index of refraction at any temperature to the value of the index at a reference temperature, generally room temperature.

Thus the device referred to herein can be considered to be a retractometer capable of indicating the index of refraction of a fluid referred to or reduced to a predetermined reference temperature.

However, even utilizing such empirical formulas, it is not always possible to obtain accurate values and clearly, without complex electronic circuitry, reduced refractive index measurements cannot be obtained.

Electronic equipment, containing transfer functions, including data or the like for modifying the input signal from the detector in response to a measured temperature to yield a refractive index corrected to a reference temperature, is extremely complicated and costly, being useful only for industrial applications in which expensive equipment may be utilized readily.

There are, however, many cases in which it may be desirable to utilize refractive index measurements and in which such expensive equipment may be impractical or prohibitively costly. For example, if one wishes to determine the state of charge of a storage battery utilizing a liquid electrolyser, one may use a refractometer since the refractive index is a measure of sulfuric acid concentration in a lead acid battery and hence reflects the state of charge.

In practice, a low cost apparatus capable of conveniently and efficiently measuring the refractive index of an acid electrolyte for lead-acid storage batteries has been unknown in the art.

OBJECTS OF THE INVENTION

It is the principal object of the present invention to provide an improved refractometer whereby disadvantages of earlier devices for measuring refractive index are avoided.

Another object of the invention is to provide a low cost and high precision device for measuring the index of refraction of a liquid referred to a predetermined temperature.

Still another object of this invention is to provide a simple, easily operated and accurate refractometer which is highly versatile in its applications and does not require complex electronic paraphernalia to correct for differences in the measurement temperature from the reference temperature.

SUMMARY OF THE INVENTION

These objects and others which will become apparent hereinafter are attained in accordance with the invention in a device for determining the index of refraction of a fluid reduced to a reference temperature, which comprises a housing or body formed with an optical probe constituted with a light-conductive path having a light-input end, light-output end, and a portion between these ends adapted to be immersed in the liquid whose effective index is to be determined, this intermediate portion or section being preferably bent (alternating curvatures) so that the critical angle of refraction and reflection varies with the index of refraction of the liquid and the light traversing this section can be measured.

At the input end of a path, a light source is provided for introducing light energy into the inlet section, while the outlet section of the light conductor is provided with a light detector, preferably generating an electric signal whose magnitude is a function of the index of refraction and hence the intensity of the light emerging from the outlet section of the path.

According to the invention, the light source is connected with the fluid (i.e. is in thermally conductive relationship therewith) so that the light source is brought to the same temperature as that of the fluid, the light source being selected so as to have a temperature coefficient of luminosity that it delivers a light intensity which varies inversely with temperature and according to a law designed to compensate the variations in the light intensity appearing at the outlet section and hence the variations of the index of refraction of the fluid as a function of temperature.

The advantage of the device of the present invention is that its use eliminates the need for any correction element. The operation of the device of the invention thus depends only upon the selection of a light source capable of emitting light of variable intensity, the variation in intensity with temperature corresponding to an inverse relationship to the coefficient of temperature of the index of refraction of the liquid.

Thus the light which appears at the outlet of the probe has an intensity which is a function essentially only of the variations of the index of refraction of the liquid and is independent of variations in this index with deviations from the predetermined or reference temperature.

The device is simple, of low cost and high reliability.

Especially important is the fact that the device of the invention can be manufactured in large numbers, e.g. by mass production or serial production for widespread applications and nevertheless with a remarkable precision. In addition, the principles can be utilized for industrial scale apparatus and for devices for measuring index of refraction with the precisions required in industry and other branches of technology.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
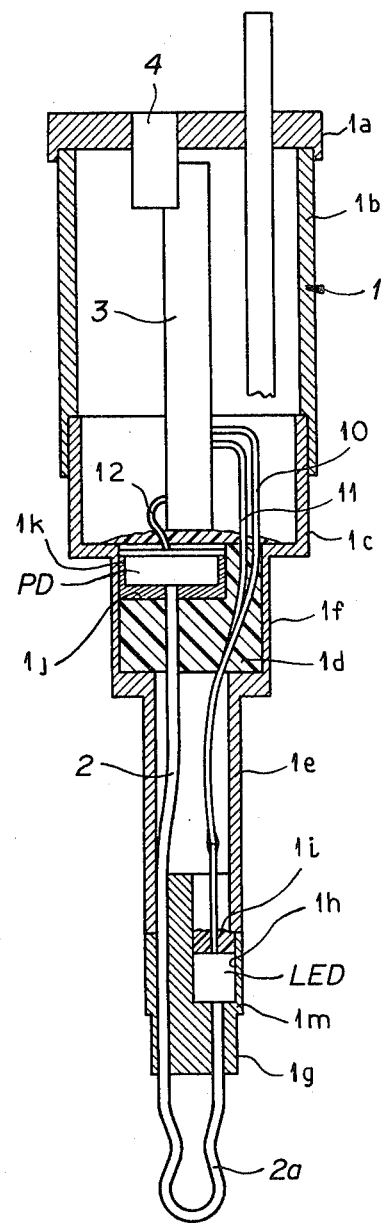
FIG. 1 is a longitudinal (axial) cross-sectional view of the device in accordance with the present invention.

FIG. 1 shows a probe adapted to measure the index of refraction of a liquid, reduced to a reference temperature or referred to this predetermined temperature, generally room temperature (e.g. 20° C.).

This probe comprises a sealed vessel 1 which can receive or be secured to an optical fiber system which comprises an optical fiber 2 having a portion 2a extending out of the lower portion of the vessel 1 to form a loop having portions of alternating curvature (concave and convex) or generally as described, for example, in the above-identified application or European patent 0 00 319 so that the light transmitted through the optical fiber is partly refracted and partly internally reflected such that the intensity of the conducted light represents a measure of the index of refraction of the liquid in contact with the surface of the projecting portions of the loop.

The vessel 1 comprises a cup 1a which can be press-fitted or thermally bonded to a sleeve 1b, the lower end of which is threaded or press-fitted onto a cup portion 1c at the upper end of a cylindrical body 1f from which the tubular portion 1a extends. A mass of electrically insulating material, shown at 1d, forms a putting agent for securing the parts in place within this body. A plug 1g is fitted into the lower end of the tubular portion 1e to secure the loop 2a in place.

One end of the optical fiber 2 terminates at an electroluminescent light source, namely, a light-emitting diode LED, the latter being received in a compartment 1h of the plug 1g and held in place by insulating potting material 1i.

The other end of the optical fiber is juxtaposed by a light-intensity detector such as a photodiode PD which is received in a compartment 1j in the potting material 1d and held in place by a bonding mass 1k.

Because the loop 2a is proximal to the light-emitting diode LED, the portion of the optical fiber proximal to the light source is adapted to be immersed in the liquid whose index of refraction is to be measured. Since the plug 1g and the lower end of tube 1e is likewise immersed in the liquid and the wall 1m separating the light-emitting diode from the liquid is of relatively small thickness, the light-emitting diode is substantially at the same temperature as the liquid whose refractive index is to be measured.

The various potting materials can be epoxy resins.

The conductors running to the LED are represented at 10 and 11 and serve to connect the LED to an electric current source, while the photodiode output is detected by the conductors represented at 12.

The electroluminescent diode LED and the photodiode PD are connected in an electronic circuit 3 which is not described in greater detail since such circuitry is known in the art as will be apparent from the aforementioned application. Eventually such circuitry maintains a constant energization of the electroluminescent source and measures the output of the photodiode. The circuit 3 can be connected via a socket or plug 4 to a display or recording unit of any conventional design.

In order to measure the index of refraction of a liquid independent of the variation in temperature thereof, it is necessary to select a probe having an electroluminescent diode LED which compensates by reducing the intensity of the outputted illumination for a given energization voltage or current as the temperature of liquid increases, the reduction corresponding to the change in the index of refraction of the liquid.

The index of refraction of partically all liquids decreases as temperature increases with a coefficient of temperature dn/dT of about $-2 \times 10^{-4}/°$ C. to $-6 \times 10^{-4}/°$ C. as measured with a fiber whose temperature coefficient itself is negligible, such as a glass fiber. Thus as the transmitted luminous intensity increases within the fiber, an automatically compensatory reduction in the light emitted by the diode LED is effected.

Hence, by varying the luminous output in direct response to the temperature of the liquid by virtue of the maintenance of the LED at the same temperature as the liquid, an automatic compensation for the temperature coefficient of the index of refraction is obtained.

This can be done precisely since the temperature coefficient of the fiber, especially when it is composed of glass, can be negligible or utilized as described below.

The luminous intensity of the diode LED is an exponential function of the temperature.

$$I = I_0 \exp(-aT)$$

Where
I = luminous intensity and
a = slope or declivity (constant).

The variation of luminous intensity emitted by the diode LED as a function of temperature is thus:

$$dI/dT = -a I \quad (1)$$

The variation of the luminous intensity of the probe is given by:

$$\left(\frac{dI}{dT}\right) = \left(\frac{dn}{dT}\right)_{eff} \cdot \left(\frac{dI}{dn}\right)$$

where (dI/dn) is the slope or declivity or the sensitivity of the probe as a function of the index of refraction and the effective coefficient $(dn/dT)_{eff}$ is defined by the equation:

$$\left(\frac{dn}{dT}\right)_{eff} = n_l \left[\frac{1}{n_l} \frac{dn_l}{dT} - \frac{1}{n_f} \frac{dn_f}{dT}\right] \quad (2)$$

where
$n_l$ = the index of refraction of the liquid, and
$n_f$ = the index of refraction of the optical fiber.

If one then takes into consideration the presence of the alternate-sense curvatures of the loop 2a of the probe, one obtains:

$$I = I_0 \exp(-cn)$$

c = slope or declivity (constant).

Thus $$dI/dn = -cI;$$

this gives $$dI/dT = c\left(\frac{dn}{dT}\right)_{eff} \cdot I \quad (3)$$

Comparing equations (1) and (3) it can be seen that the temperature effect can be annulled if $$a = -c\left(\frac{dn}{dT}\right)_{eff}$$

If the numerical values for the equations (1) and (3) are the same there will be no variation in luminous intensity as a function of temperature.

EXAMPLE $a = 8 \times 10^{-3}/°$ C. for an electroluminescent diode of gallium arsenide doped with aluminum (Ga As: Al) ESBR 5501 manufactured by Stanley Electric Co., Yokohama, Japan, $(dn/dT)_{eff} = -1.4 \times 10^{-4}/°$ C. in the case of a polystyrene fiber whose temperature coefficient is $-1.3 \times 10^{-4}/°$ C. immersed in an electrolyte of a lead-acid storage battery, i.e. a sulphuric acid electrolyte having a density of 1.25. The temperature coefficient of the latter is $-2.5 \times 10^{-4}/°$ C. as calculated by formula (2).

Figure 2:
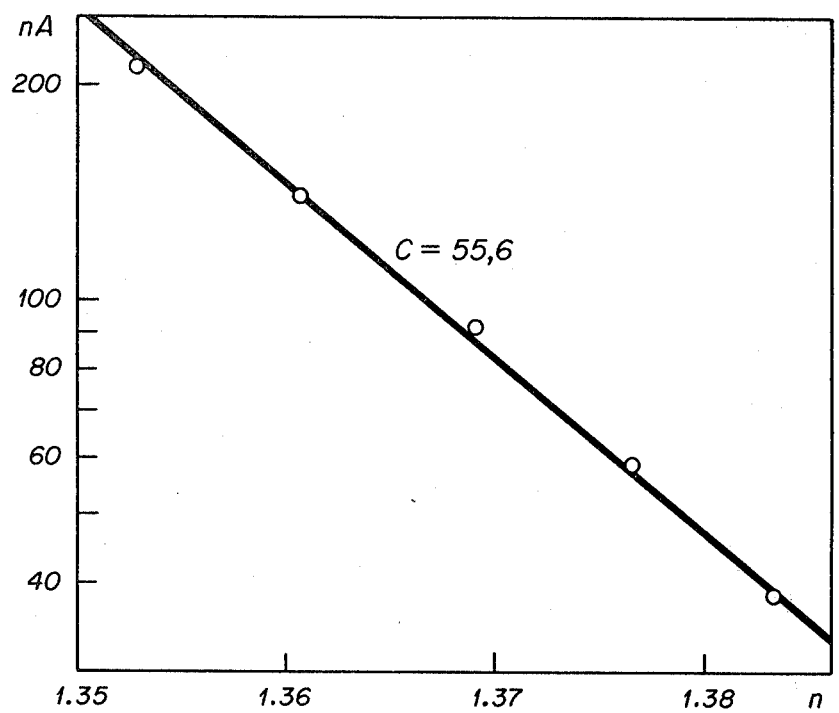
FIG. 2 is a graph on a semilogarithmic scale in which the output electric current in nanoamperes is plotted along the ordinate while the index of refraction is plotted along the abscissa, showing the application of the invention to the determination of index of refraction and hence the variation of the output with transmitted light at the different indices of refraction.
Figure 3:
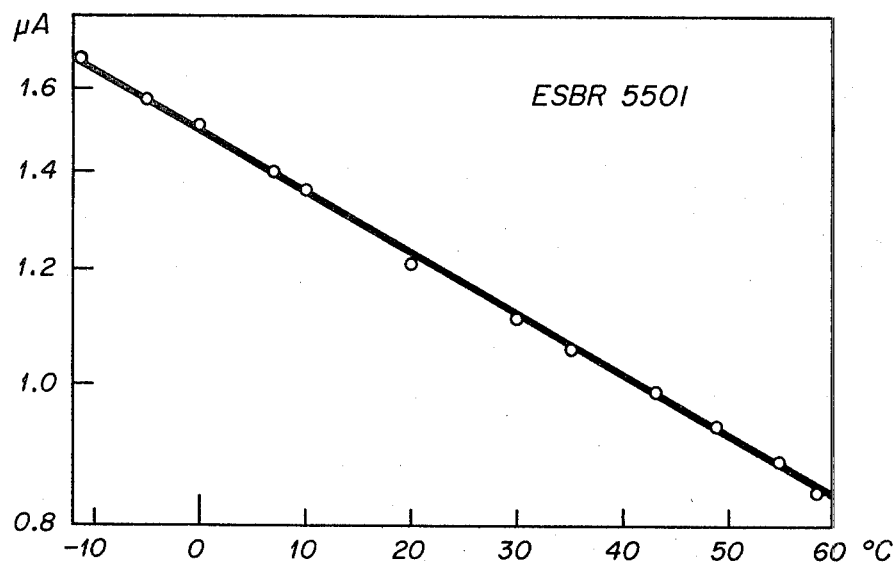
FIG. 3 is a diagram illustrating the temperature dependency of the luminous intensity of an electroluminescent diode coupled with an optical fiber in accordance with the invention (output in microamperes plotted along the ordinate vs temperature in ° C. plotted along the abscissa).

This corresponds to the diagram shown in FIG. 2 in which the current measured by the photodiode of FIG. 1 is plotted along the ordinate as a function of the indices of refraction of different liquids measured at 20° C. and plotted along the abscissa so that the constant c is:

c = 55.6/refractive index $$\left(\frac{dn}{dT}\right)_{eff} = -1.4 \times 10^{-4}/°C.$$

$$c\left(\frac{dn}{dT}\right)_{eff} = -7.8 \times 10^{-3}/°C.$$

The table below shows the variations of the current recorded by the photodetector PD for the probe of FIG. 1 immersed in a solution of known index of refraction at different temperatures. The variations noted for the different measured indices are the following:

For n = 1.3528, Δi = 0.057 nA/° C.;

TABLE

| Solution Temperature (°C.) | Current PD (× 10⁻⁷ A) | | |
|---|---|---|---|
| | n = 1.3528 | n = 1.3690 | n = 1.3833 |
| −9.3 | 2.16 | 0.845 | 0.365 |
| −5.0 | 2.15 | 0.89 | 0.36 |
| 5.0 | 2.17 | 0.91 | 0.38 |
| 17.5 | 2.22 | 0.96 | 0.395 |
| 25.0 | 2.22 | 0.99 | 0.42 |
| 30.0 | 2.23 | 0.99 | 0.42 |
| 35.5 | 2.26 | 1.00 | 0.425 |
| 40.0 | 2.22 | 0.99 | 0.425 |
| 45.0 | 2.20 | 1.00 | 0.42 |
| 50.0 | 2.20 | 1.00 | 0.43 |
| 60.0 | 2.18 | 1.00 | 0.45 | for n = 1.3690, Δi = 0.22 nA/° C.
for n = 1.3833, Δi = 0.12 nA/° C.

These results demonstrate excellent stability of the probe between −10° C. and +60° C. with respect to the index of refraction of the liquid.

Comparing the results with FIG. 2, it can be seen that at 20° C.:
n = 1.3528 gives i = 2.18 nA;
at 30° according to the formula $(dn/dT)_{eff}$:
Δn = 0.0014 thus n = 1.342 corresponding to i=202 nA;

similarly, $\Delta i = 1.6$ nA/° C. compared with $\Delta i = 0.057$ nA/° C.

The literature shows that many types of electroluminescent diodes have been developed in the art and that these electroluminescent diodes have various temperature dependencies with outward powers diminishing with temperature in proportions and with curves neighboring the dependency of the diode utilized in the specific example given earlier. For example, gallium phosphide diodes doped with zinc oxide (GaP: ZnO) or gallium arsenide diodes doped with silicon (GaAs: Si).

Any necessary further compensation, e.g. to make up for over- or undercompensation, can be obtained by selecting the material forming the optical fiber as a function of its temperature coefficient so that the effective coefficient $(dn/dT)_{eff}$ has the desired value.

When the coefficient of temperature of the optical fiber is nonnegligible, therefore, it provides a contribution to the effective coefficient.

The wide range of optical fibers and electroluminescent diodes available permits any combination to be assembled to obtain any desired compensation for the temperature coefficient of the index of refraction of any particular liquid to be measured.

The luminous intensity registered by the photodetector PD can be used to display or indicate the index of refraction of the liquid referred to the predetermined reference temperature or to any physical parameter of which the index of refraction is in turn a measure.

For example, when the device is used to determine the index of refraction of the electrolyte of a vehicle-starting battery, the apparatus can display the density of the electrolyte directly without any correction for temperature. It is also possible to display, via suitable indicia, whether the battery is at full or partial charge or in a state of discharge. The output of the device can be amplified by conventional circuitry and the signal-processing circuitry can include means for displaying an indication which is directly proportional to the state of charge in spite of the fact that the charge state is not a linear function of the index of refraction of the electrolyte.

I claim:

1. A device for determining the index of refraction of a fluid reduced to a predetermined reference temperature, comprising:

a housing;

an optical fiber mounted on said housing and having a sensor portion projecting from said housing and formed with alternating curvatures for introduction into a fluid whose index of refraction is to be measured;

a light-intensity detector connected to one end of said optical fiber for measuring the luminous intensity transmitted through said optical fiber; and a light source in said housing positioned to lie in thermally conductive relationship with said fluid whereby said source is substantially at the same temperature as said fluid, said source having a temperature coefficient of luminous output such that its luminous output varies inversely with temperature according to a law which compensates the luminous output of said source for variation in the index of refraction of said fluid as a function of the temperature.

2. The device defined in claim 1 wherein said optical fiber consists of a material whose temperature coefficient is negative and such that it is additive to the variations of luminous output of said source to obtain the degree of compensation required for the variation in the index of refraction of the fluid as a function of temperature.

3. The device defined in claim 1 wherein said source is a light-emitting diode.

4. The device defined in claim 1, claim 2 or claim 3 wherein said detector is a photodiode.

5. The device defined in claim 4 wherein said housing comprises a sealed receptacle containing electrical circuitry connected to said source and said detector, and a tubular member extending from said vessel, said source being mounted in said tubular member, said optical fiber having a loop projecting from said tubular member adjacent said source.

* * * * *